(12) United States Patent
Mizutani

(10) Patent No.: US 7,098,373 B2
(45) Date of Patent: Aug. 29, 2006

(54) IL-18 TRANSGENIC ANIMAL

(75) Inventor: Hitoshi Mizutani, 10-41, Oozono-cho, Tsui-shi Mie (JP) 514-0046

(73) Assignees: Hitoshi Mizutani, Tsu (JP); Kenji Nakanishi, Takarazuka (JP); Taiho Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 10/482,662

(22) PCT Filed: Jul. 11, 2002

(86) PCT No.: PCT/JP02/07047

§ 371 (c)(1),
(2), (4) Date: Jan. 5, 2004

(87) PCT Pub. No.: WO03/005811

PCT Pub. Date: Jan. 23, 2003

(65) Prior Publication Data

US 2004/0187171 A1  Sep. 23, 2004

(30) Foreign Application Priority Data

Jul. 12, 2001  (JP) .............................. 2001-212218

(51) Int. Cl.
*A01K 57/00* (2006.01)
*A01K 67/033* (2006.01)
*A01K 67/027* (2006.01)
*G01N 33/00* (2006.01)
*C12N 15/00* (2006.01)

(52) U.S. Cl. .................... 800/3; 800/9; 800/18; 800/21
(58) Field of Classification Search .................... 800/3, 800/18, 21; 536/23.1
See application file for complete search history.

(56) References Cited

FOREIGN PATENT DOCUMENTS

WO         01/95710         12/2001

OTHER PUBLICATIONS

Mee et al. (2000, British Journal of Dermatology, 143: 330-336).*
Gerlai (1996, Trends in Neuroscience, 19:177-181).*
Ackermann et al. (1999, British Journal of Dermatology, 140: 624-633).*
Kremer et al. (1999, Journal of Immunology, 163: 3226-3231).*
Mullins and Mullins (1996, J. Clin. Invest, 97: 1557-1560).*
Hammer, et al. (1990, Cell 63:1099-1112).*
Yamanaka K. et al., "Skin-Specific Caspase-1-Transgenic Mice Show Cutaneous Apoptosis and Pre-Endotoxin Shock Condition With a High Serum Level of IL-18[1]". The Journal of Immunology,vol. 165, pp. 997-1003 2000.
Hoshino T. et al., "Cutting Edge: IL-18-Transgenic Mice: In Vivo Evidence of a Broad Role for IL-18 in Modulating Immune Function". The Journal of Immunology, vol. 166, pp. 7014-7018 Jun. 15, 2001.
Osaki T. et al., "Potent antitumor effects mediated by local expression of the mature form of the Interferon-γ inducing factor, Interleukin-18(IL-18)." Gene Therapy, vol. 6, pp. 808-815 1999.
Immunology 1997-1998, pp. 62-72 with Chemical Abstracts 127:246739d, vol. 121, No. 18 1997.
Clinical Immunology, vol. 30, No. 2, pp. 191-198, 1998(With partial English Translations).
Yamanaka K. et al., "Skin-Specific Caspase-1-Transgenic Mice Show Cutaneous Apoptosis and Pre-endotoxin Shock Condition With a High Serum Level of IL-18[1]". The journal of Immunology, vol. 165, pp. 997-1003 2000.
Tomohiro Yoshimoto, et al., "IL-18 induction of IgE: dependence on CD4+ T cells, IL-4 and STAT6", Nature Immunology, vol. 1, No. 2, Aug. 2000, pp. 132-137.

* cited by examiner

*Primary Examiner*—Anne M. Wehbe'
*Assistant Examiner*—Joanne Hama
(74) *Attorney, Agent, or Firm*—Oblon, Spivak, McClelland, Maier & Neustadt, P.C.

(57) ABSTRACT

Transgenic non-human mammals comprising a DNA with an exogenous IL-18 gene incorporated in it such that the exogenous IL-18 gene is skin-specifically expressed, or their offsprings.

The transgenic non-human mammals according to the present invention spontaneously develop atopic dermatitis under specific pathogen-free conditions, and therefore, are useful as disease model animals. Use of the transgenic non-human mammals according to the present invention makes it possible to develop drugs for preventing or treating atopic dermatitis by natural immunity and also to elucidate the onset mechanisms of atopic diseases.

19 Claims, 4 Drawing Sheets

1. KIL−18Tg
2. WT

A. PTH–IL18 RT PCR
B. mG3PDH

1. λ Hind
2. KIL–18Tg
3. Normal
4. PCR positive control

IL-18 TRANSGENIC ANIMAL

TECHNICAL FIELD

This invention relates to transgenic animals useful as model animals of atopic dermatitis, especially chronic atopic dermatitis.

BACKGROUND ART

Atopic diseases such as atopic dermatitis, asthma, allergic rhinitis and allergic conjunctivitis are diseases which respond hypersensively to environmental antigens or the like, to which normal subjects do not respond, and develop destruction or disorder of various organs by their own immune system. Th2 cytokines which enhance allergic responses are assumed to play a role in the onset mechanism of these diseases. Elucidation of their induction and regulatory mechanisms, therefore, has an important significance from the standpoints of physiology and pharmacology, but these mechanisms have not been clarified in detail yet.

Treatments of atopic diseases are currently known to include primarily those which rely upon avoidance from antigens, or antihistamines which compete with binding of mediators such as histamine to receptors, or anti-inflammatory steroidal agents. Development of treatment methods directed to more specific acting mechanisms is, however, hampered due to lack of appropriate laboratory animals.

Induction of an allergic response on a laboratory animal has conventionally required administration of an antigen or allergen to the animal after sensitizing the animal beforehand by repeated immunization of the animal with the antigen or allergen. In this case, simultaneous sensitization of many animals, however, requires a great deal of labor and further, may produce variations in reactivity among the individual animals, leading to a problem in the reproducibility of an experiment.

In recent years, NC/Nga mouse is attracting interests as a model animal for atopic dermatitis. Dermatitis which occurs on this mouse, however, leads to its onset for the first time in the presence of mites, and moreover, its onset rate is unstable and its symptom varies.

Laboratory animals are indispensable for the development of medicines for atopic diseases, leading to a strong outstanding desire especially for model animals of atopic dermatitis. These days, however, there is not any atopic dermatitis model animal available and provided for practical use, which has been established in genetic background, is immunologically defined and is usable for the development and research of various treatment methods and drugs under specific pathogen-free conditions.

An object of the present invention is, therefore, to create an animal useful as an atopic dermatitis model.

DISCLOSURE OF THE INVENTION

The present inventors were hence interested in interleukin 18 (IL-18). IL-18 is subjected to processing by a protease called "caspase 1" (IL-1β converting enzyme)" and is converted from the precursor type to the mature type. Functions of mature IL-18 are known to include (1) induction of IFN-γ production, (2) potentiation of Fas-mediated apoptosis by enhancement of Fas ligand expression, (3) induction of GM-CSF, and (4) inhibition of IgE production by coexistence of IL-12. Further, IL-18 is also expressed in various tissues other than immune tissues, such as osteoblast-like interstitial cells, keratinocytes, intestinal epithelial cells, adrenocortical cells and pituicytes, and active research have been being conducted on its physiological roles [see Men-eki (Immunology) 1997–98, 62–72, Nakayama-Shoten Co., Ltd.; Rinsho Men-eki (Clinical Immunology) 30(2), 191–198 (1998); etc.]. In recent years, the present inventors found that, when IL-18 is solely overexpressed, production of IL-4 and IL-13 is enhanced to induce production of IgE. This means that IL-18 is deeply associated with a Th2 cytokine which plays a role in the onset of an atopic disease. The present inventors, therefore, considered that creation of model animals with promoted secretion of caspase 1, which converts IL-18 to the mature type, would be useful for the elucidation of the onset mechanisms of atopic diseases and the development of treatment methods for atopic diseases. However, caspase 1 is an apoptosis-inducing enzyme, and therefore, is accompanied by a problem in that not only secretion of IL-18 but also development of apoptotic effects takes place when it is expressed in a living body by introduction of its gene.

From the foregoing viewpoint, the present inventors created a transgenic non-human mammal with a DNA incorporated such that the caspase 1 gene is skin-specifically expressed, and filed an application for patent thereon (WO 01/95710 A1) This transgenic animal shows the symptom of atopic dermatitis, and is useful as a model animal. However, this transgenic animal also developed an epidermal cell necrotic symptom and showed the symptom of acute-phase dermatitis, and in some instances, developed systemic hepatopathy upon infection to bacteria.

As a result of a further investigation, the present inventors have now found that direct introduction of a DNA, which has been obtained by recombination of mature IL-18 such that mature IL-18 is skin-specifically expressed, into an animal cell makes it possible to produce a transgenic animal which continuously secretes mature IL-18 into blood and develops the symptom of atopic dermatitis even when raised under conditions from which specific pathogen such as mites and fungi have been excluded and also that unexpectedly, the transgenic animal is free of the epidermal cell necrotic symptom and hepatopathy and is useful as a model animal of atopic dermatitis closer to human atopic dermatitis, leading to the completion of the present invention.

Specifically, the present invention provides a transgenic non-human mammal comprising a DNA with an exogenous IL-18 gene incorporated in it such that the exogenous IL-18 gene is skin-specifically expressed, or its offspring, and also, a creation method of the same.

The present invention further provides a screening method of a preventing or treating substance for atopic dermatitis, which comprises administering a test substance to the transgenic mammal to test its atopic dermatitis improving effect, and also a preventing or treating drug for atopic dermatitis, comprising a substance determined to have atopic dermatitis improving effect by the screening method.

BEST MODES FOR CARRYING OUT THE INVENTION

Figure 1:
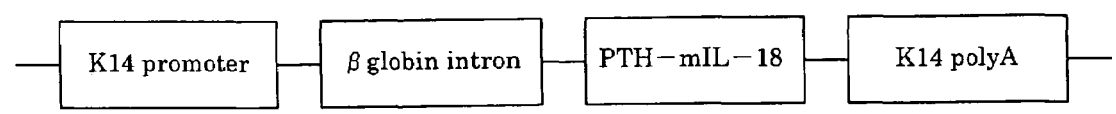
FIG. 1 schematically illustrates the linkage structure of a recombinant DNA used for introduction.

The transgenic animal according to the present invention comprises a DNA incorporated in its somatic cells or germ cells such that an exogenous IL-18 gene is skin-specifically expressed. As the exogenous IL-18 gene, a human or mouse IL-18 gene is preferred. Illustrative are genes such as human mature IL-18 (hIL-18), mouse mature IL-18 (mIL-18), human precursor IL-18 (hproIL-18), and mouse precursor IL-18 (mproIL-18). Preferred is hIL-18 or mIL-18, with 0.63 kb cDNA as the complete encoding region of mIL-18 being particularly preferred.

As the DNA with the exogenous IL-18 gene incorporated there in such that the exogenous IL-18 gene is skin-specifically expressed, a recombinant DNA containing the exogenous IL-18 gene and a promoter for a skin specific protein is preferred. The promoter for the skin specific protein can be a promoter for a protein which specifically exists in the skin. Illustrative are keratin promoters such as keratin 14, keratin 5, keratin 1 and keratin 10 and promoters for involucrin and the like, with keratin promoters being particularly preferred. For the promotion of secretion of IL-18, it is also preferred to ligate a leader sequence of a parathyroid hormone gene, for example, preproparathyroid hormone (PTH) gene to the IL-18 gene. For the skin-specific expression and good secretion of mature IL-18, it is more preferred to ligate a parathyroid hormone gene and an IL-18 gene downstream of a keratin promoter. To improve the expression efficiency of the gene, on the other hand, ligation of an intron such as β-globin intron is preferred.

The above-described DNA may preferably have a sequence ("poly A", generally called "terminator") which terminates transcription of a target messenger RNA in a transgenic mammal, and by using the sequences of individual genes derived from viruses or various mammals, for example, expression of the genes can be manipulated. Preferably, the poly A's of the above-described skin-specific proteins are used, with the poly A of keratin or the like being particularly preferred. Additionally, for the purpose of affording still higher expression of the target gene, the splicing signal and enhancer region of each gene and a portion of the intron of a eukaryotic gene may be ligated 5' upstream of the promoter region, or between the promoter region and the translational region, or 3' downstream of the translational region.

Examples of the non-human mammal usable for introducing the recombinant DNA obtained as described above can include bovine, swine, sheep, goat, rabbit, dog, cat, guinea pig, hamster, rat and mouse. Preferred are rabbit, dog, cat, guinea pig, hamster, mouse and rat. Among these, Rodentia animals such as guinea pig, hamster, mouse and rat are preferred, with mouse being particularly preferred.

The transgenic animal according to the present invention can be created, for example, by introducing a DNA, in which the above-mentioned exogenous IL-18 gene has been incorporated to skin-specifically express the exogenous IL-18 gene, into a fertilized egg of a non-human mammal and implanting the fertilized egg in a female of the mammal. As the fertilized egg, one at the stage of a male pronucleus (approximately 12 hours after fertilization) is preferred. Examples of a transfection method of the recombinant DNA can include, calcium phosphate transfection, the electric pulse method, lipofection, agglutination, microinjection, the particle gun method, and DEAE-dextran transfection, with microinjection being particularly preferred.

The fertilized egg transfected with the recombinant DNA is implanted in a female of the same species of animal as the fertilized egg. As an implanting method, artificial transplantation and implantation into the oviduct of a pseudopregnant female animal is preferred. From offsprings born from the animal with fertilized eggs implanted therein as described above, one or more individuals in each of which the target gene has been expressed can be bred over generations.

Confirmation as to whether or not the target gene is contained in each transgenic animal so obtained can be achieved by collecting its DNA from the skin and conducting an analysis for the transfected gene by polymerase chain reaction (PCR) and Southern blotting.

The transgenic animal according to the present invention obtained as described above features that, because the exogenous IL-18 gene is expressed in the skin, it develops a symptom of atopic dermatitis even under specific pathogen-free conditions and also survives for a long period.

Described specifically, the transgenic animal according to the present invention has the exogenous IL-18 gene in only the skin, and does not have it in other tissues, for example, the liver, kidney, lung, brain and spleen. As a consequence, mature IL-18 is abundantly secreted in the skin of the transgenic animal according to the present invention. Moreover, mature IL-18 is contained in a large quantity in the blood of the transgenic animal according to the present invention than in those of normal animals.

The transgenic animal according to the present invention shows a symptom of atopic dermatitis, for example, lichenified dermatitis or erosive dermatitis from about its 24 weeks of age. Of these, the symptom of lichenified dermatitis is developed as a more distinctive characteristic in the transgenic animal according to the present invention than in the above-described caspase 1 transgenic animals, thereby indicating that the transgenic animal according to the present invention develops a symptom closer to that of human chronic dermatitis.

According to an observation of skin tissues under an optical microscope, the transgenic animal according to the present invention develops an alteration, such as inflammation associated with hyperkeratosis or acanthosis, on the thick epidermis around an ulcer from about its 24 weeks of age, and in the dermis at each lesion, infiltration of monocytes and mast cells takes place. However, substantially no epidermal cell necrosis occurs. In addition, substantially no hepatopathy is observed on the transgenic animal according to the present invention. As neither epidermal cell necrosis nor hepatopathy is generally observed with human atopic dermatitis, the transgenic animal according to the present invention is appreciated to show a symptom extremely close to human atopic dermatitis.

Further, the transgenic animal according to the present invention repeats skin scratching behavior extremely frequently compared with normal animals and the above-described caspase 1 transgenic animals, and therefore, is understood to be accompanied by strong itching typical to atopic dermatitis. In addition, the transgenic animal according to the present invention shows a symptom characteristic to atopic dermatitis that blood histamine level and IgE are extremely high.

As is readily appreciated from the foregoing, the transgenic animal according to the present invention develops a symptom of atopic dermatitis under specific pathogen-free conditions, and hence, is useful as a symptom model of atopic dermatitis. Accordingly, screening of a preventing or treating substance for atopic dermatitis is feasible provided that a test substance is administered to the transgenic animal or its offspring according to the present invention to test its atopic dermatitis improving effect. This atopic dermatitis improving effect can be tested by making either single use or appropriately combined use of measurement of blood mature IL-18 level, detection of mature IL-18 in the skin, visual observation, microscopic observation of a skin tissue, measurement of blood histamine level and like methods as described above. Further, any test substance determined to possess atopic dermatitis improving effect by the screening is useful as a drug for the prevention or treatment of atopic dermatitis.

EXAMPLES

The present invention will next be described in further detail based on Examples. It should, however, be borne in mind that the present invention is by no means limited to the following Examples.

Firstly, a description will be made about various testing methods and materials employed in the Examples.

(1) Northern Blotting cDNA of mIL-18 was obtained from Hyogo College of Medicine (Dr. Okamura) [Nature 378, 88–91, (1995)]. From tissues of an mIL-18 transgenic mouse (KIL-18Tg), which was obtained in Example 1 to be described subsequently herein, and a control mouse, total RNA was extracted using "Isogen Reagent" (product of Nippon Gene Co., Ltd.). In a Northern blot analysis, the total RNA (10 µg) was fractionated in size by electrophoresis on 2 wt. % formaldehyde/agarose gel. RNA was transferred to a nylon membrane ("Immobilon-N", product of Millipore Corporation), and $^{32}$P-labeled cDNA corresponding to mouse IL-18 was used as a probe. Subsequent to hybridization, the blot was washed at 42° C. twice with 1×SSC/0.1 wt. % SDS and twice with 2×SSC/0.1 wt. % SDS. The blot was then exposed at −70° C. to an X-ray film.

(2) Cytokine, Cytokine Assay and Antibody

Biological activity of IL-18 was assayed in terms of IFN-γ inducing activity by using IL-18-responsive mouse NK cells. Recombinant mouse IL-18 (rmIL-18), a rabbit anti-mouse IL-18 neutralizing antibody and a mouse IL-18 ELISA kit were obtained from Hayashibara Biochemical Laboratories, Inc. With the mouse IL-18 ELISA kit, 10 to 1,000 pg/mL of IL-18 were detectable.

(3) Immunohistochemistry

Biopsy samples from the transgenic and wild-type mice were fixed for 2 hours with a phosphate-buffered formaldehyde solution, followed by cutting into paraffin slices. The samples were immediately frozen in "OCT Compound" (product of Miles Inc.), a frozen tissue matrix, and stored at −70° C. Cryostat sections (5 µm) were fixed at 4° C. for 5 minutes in acetone, and incubated for 1 hour with an appropriately-diluted primary antibody. After washing, the bound primary antibody was visualized with AEC (product of DAKO JAPAN CO., LTD.) as a substrate while using "Vectastein Elite Kit" (product of Vector Laboratories, Inc.).

(4) Immunoblotting

Immunoblotting was conducted following J. Clin. Invest. 87, 1066 (1991). After DNA and RNA were removed using "Isogen Kit", a lysate of epidermal cells from the transgenic and control mice was suspended with SDS-sample buffer under reducing conditions. Electrophoresed proteins were transcribed onto a nitrocellulose membrane (product of Scheicher & Schuell GmbH) by using a semidry blotter (manufactured by Bio-Rad Laboratories, Inc.). Subsequent to incubation of the membrane with the primary antibody for 1 hour, the proteins were subjected to secondary incubation with alkali-phosphatase-labeled anti-mouse IgG or anti-rabbit IgG antibody, and finally, were visualized with a Western Blue substrate (product of Promega Corporation).

Example 1

(1) DNA Structure, and Generation of Transgenic Mice 0.63 kb cDNA of the complete encoding region of mIL-18, said cDNA having been ligated with the prepro parathyroid hormone leader sequence (PTH) and having been obtained from Dr. Tahara, The Institute of Medical Science, The University of Tokyo [see Genetherapy 6, 808–815 (1999)], was ligated by blunt end ligation to the keratin 14 promoter [obtained from Dr. E. Fuchs, The University of Chicago; see Nature 374, 159 (1995)] and the rabbit β-globin intron [obtained from Dr. Tanaka, Kyoto University; see Nature 374, 159 (1995)] (FIG. 1: In FIG. 1, "K14 promoter" indicates the keratin 14 promoter, "β globin intron" the rabbit β-globin intron, "PTH-mIL-18" the 0.63 kb cDNA of the complete encoding region of mIL-18 ligated with PTH, and "K14 poly A" the human keratin 14 poly A). Following the procedure described in Dev. Growth Differ. 39, 257 (1997), the resulting DNA fragment was injected into fertilized eggs of a C57BL/L6 mouse (Charles River Japan, Inc.) by microinjection.

(2) Confirmation of Overexpression of mIL-18 in the Skin of Transgenic Mice

Relying upon the presence of the transfected gene by PCR and Southern blotting making use of DNA from the caudal skin, offsprings were screened. Of the 50 mice born in total, two mice (♂2) were transgenic of mIL-18 (hereinafter abbreviated as "KIL-18Tg"). KIL-18Tg were healthy from the time of birth, and grew normally. Before 24 weeks of age, however, they were a little smaller than the wild-type littermates. After that time point, a symptom of chronic-active dermatitis was clearly developed on KIL-18Tg. As a result of crossing of those two ♂KIL-18Tg with wild-type ♀, KIL-18Tg and wild-type offsprings were born at ♂:♀=1:1. The all experiments were each conducted by a comparison between non-transgenic or wild-type littermates and heterozygotes with the transfected gene passed over generations.

(3) Skin Conditions

In the case of KIL-18Tg, from the 24$^{th}$ week under conditions that no particular pathogen was detected, moderate dermatitis around the eyes became profound, and then rapidly proceeded to extensive dermatitis. In subsequent several weeks, those symptoms spread to the face, ears, neck, body and legs. The skin inflammation became chronic so that skin dermatitis continued. Hair on the face, trunk and extremities were lost with many traces of scratches.

At the level of an optical microscope, no particular histomorphological alteration was observed on the skins of KIL-18Tg up to the 24$^{th}$ week. On the thick epidermals at lesions of 24-week-old KIL-18Tg, however, chronic-eczema-like alterations accompanied by lichenification were observed. The dermises at the lesions were infiltrated with numerous monocytes and mast cells. No necrosis of epidermal cells was observed.

IL-18 was detected at high level in thick epidermal tissues of KIL-18Tg. In the control mice, on the other hand, IL-18 was detected only at trace level.

(4) Detection of Mature IL-18 in the Skin

Figure 2:
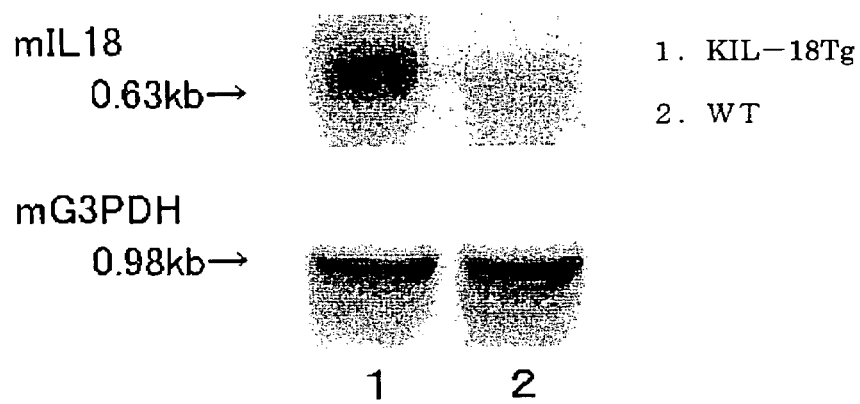
FIG. 2 electrophoretogrammatically shows the results of expression of mRNA of mature IL-18 (mIL-18) in the ear epidermal tissue of keratinocyte specific IL-18 transgenic mouse (KIL-18Tg) as analyzed by Northern blotting.
Figure 3:
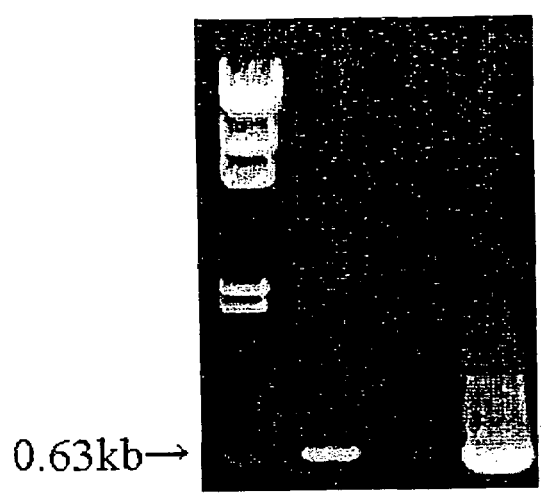
FIGS. 3 A and B electrophoretogrammatically presents expression of mRNA of mIL-18 in the ear epidermal tissue of KIL-18Tg as analyzed by PT-PCR.

By Northern blot analysis and RT-PCR, mRNA of mIL-18 in the ear epidermal, dorsal epidermal, liver, kidney, colon, lung, brain and spleen of each KIL-18Tg was measured. As a result, 0.63 kb mIL-17 mRNA was confirmed to exist only in the ear and dorsal surfaces of KIL-18Tg, but was not confirmed to exist in the other tissues (liver, kidney, colon, lung, brain and spleen) (see FIGS. 2 and 3). In FIG. 2, lane 1 shows the detection results of mRNA in the ear epidermal tissue of one of KIL-18Tg, while lane 2 indicates the detection results of mRNA in the ear epidermal tissue of one of the non-transgenic (wild-type) littermates. In FIG. 3, on the other hand, lane 1 corresponds to λ Hind, lane 2 to KIL-18Tg, lane 3 to a normal mouse, and lane 4 to a positive control.

(5) Blood IL-18 level

Figure 4:
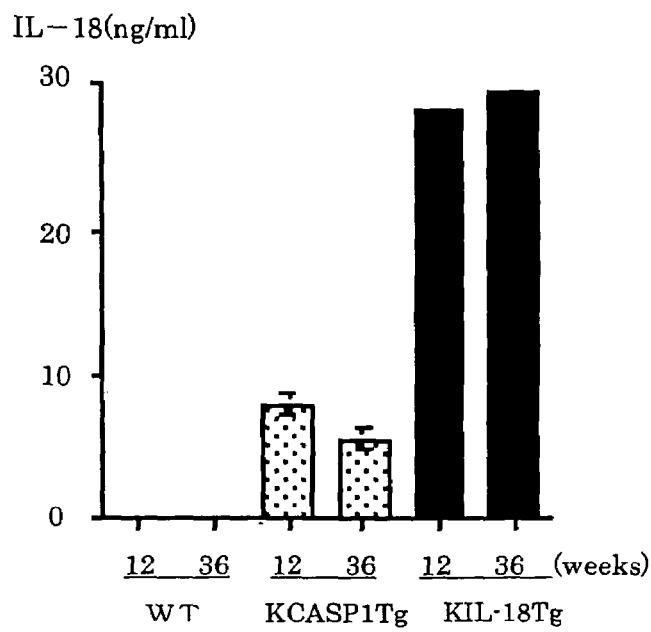
FIG. 4 histogrammatically depicts changes in the serum levels of IL-18 in KIL-18Tg, keratinocyte specific caspase-1 transgenicmouse (KCASP1Tg) and the wild-type (WT) at 12 weeks and 36 weeks after birth.

An investigation was conducted as to whether or not localized activation of IL-18 by an exogenous IL-18 will result in systemic accumulation of mature cytokine. As shown in FIG. 4, high-level existence of IL-18 was significantly recognized in sera of KIL-18Tg at 12 weeks and 36 weeks after birth. In contrast, the serum IL-18 level remained low in the wild-type (WT) littermates throughout their lifetime (0.1 ng/mL or lower) The serum IL-18 level of each KIL-18Tg retained high value. FIG. 4 also shows the serum IL-18 level of a transgenic mouse with a DNA incorporated therein such that the caspase 1 gene would be skin-specifically expressed (see WO 01/95710 A1, KCASP1Tg). The serum IL-18 level of each KIL-18Tg was extremely higher than that of KCASP1Tg.

To ascertain that IL-18 in the serum of KIL-18Tg is mature IL-18, IL-18 in the serum of one of KIL-18Tg was investigated for biological activities. As a result, the serum from KIL-18Tg was found to have ability to induce production of IFN-γ by natural killer cells cloned with IL-18 responsiveness. Further, this IFN-γ inducing ability was completely inhibited by the anti-IL-18 antibody (neutralizing antibody). This means that active IL-18 is contained in the serum of KIL-18Tg. However, IFN-γ was not detected in the serum of KIL-18Tg in steady state. As appreciated from the foregoing, KIL-18Tg continuously secreted mature IL-18 in the circulating blood.

(6) Skin Scratching Behavior by Transgenic Mice

Number of skin scratching by KIL-18Tg and the wild-type (C57BL/L6 mouse) were visually counted during 60 minutes.

Figure 5:
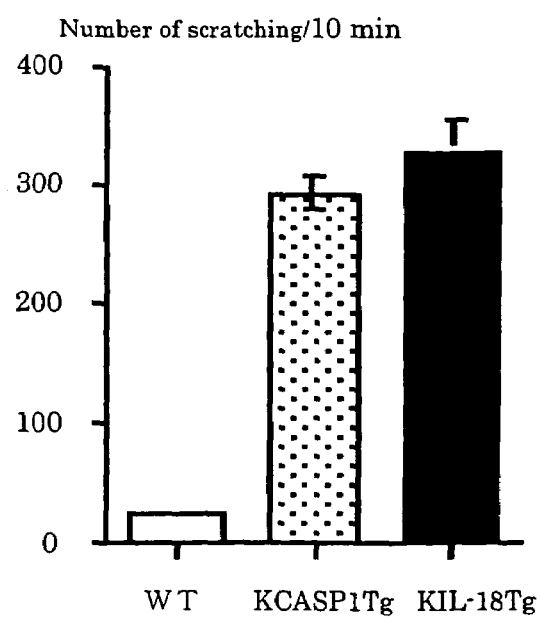
FIG. 5 histogrammatically shows the test results of number of skin scratching by KIL-18Tg, KCASP1Tg and the wild-type (WT).

As a result, as illustrated in FIG. 5, the number of scratching by the wild-type was 50 episodes or fewer per 10 minutes while that by KIL-18Tg was 300 episodes or more per 10 minutes. It was, therefore, found that severe dermatitis associated with itching occurred on the transgenic mouse according to the present invention. Further, the number of episodes of scratching by KIL-18Tg was greater than that by KCASP1Tg.

(7) Blood IgE Level

Figure 6:
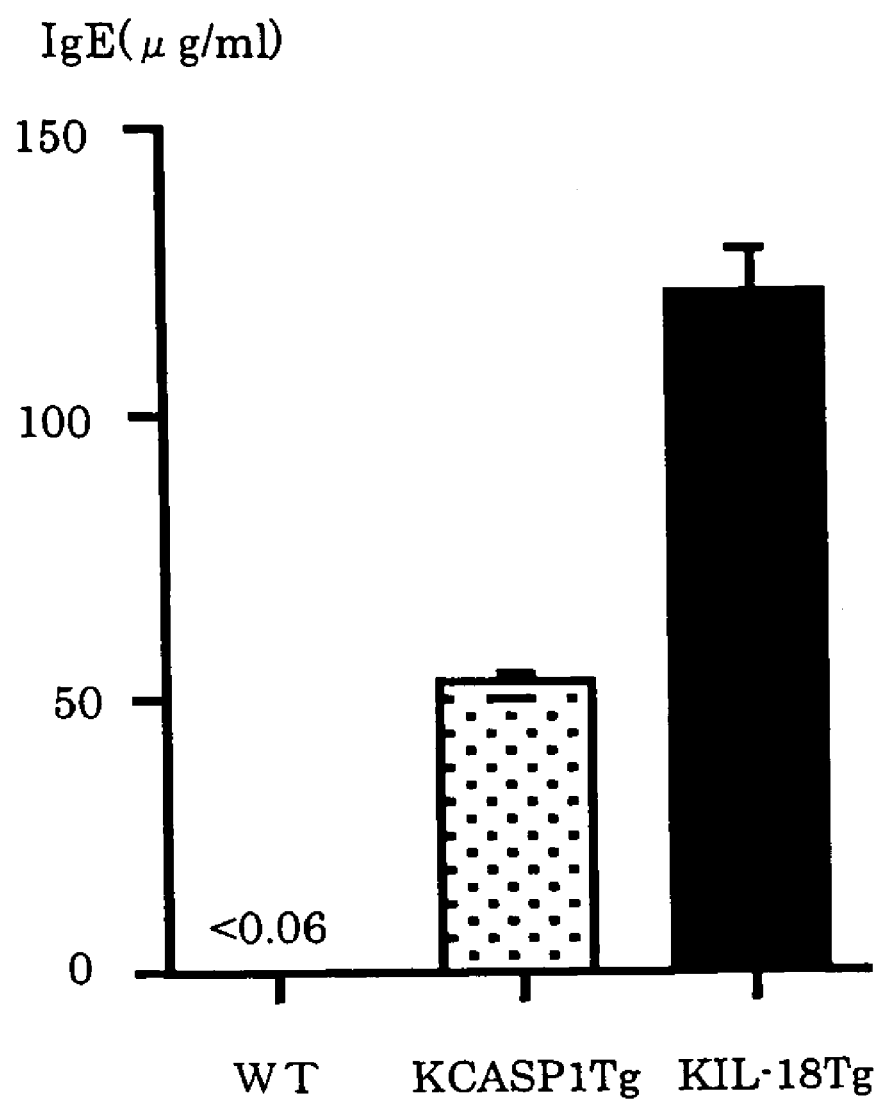
FIG. 6 histogrammatically depicts blood levels of IgE in KIL-18Tg, KCASP1Tg and the wild-type (WT) (at 36 weeks)

Blood IgE levels (ELISA) of KIL-18Tg and the wild-type were measured at 36 weeks of age. The results are shown in FIG. 6. From the results, it is understood that in the case of the transgenic mouse according to the present invention, the blood IgE level reaches 120 μm/ml or higher, i.e., an extremely high value at 36 weeks of age. In addition, the blood IgE level of KIL-18Tg was extremely higher than that of KCASP1Tg.

INDUSTRIAL APPLICABILITY

The transgenic non-human mammal according to the present invention spontaneously develops atopic dermatitis under specific pathogen-free conditions, and therefore, is useful as a disease model animal. Use of the transgenic animal according to the present invention makes it possible to develop drugs for preventing or treating atopic dermatitis by natural immunity and also to elucidate the onset mechanisms of atopic diseases.

The invention claimed is:

1. A transgenic mouse whose genome contains an exogenous polynucleotide encoding murine IL-18 operably linked to a mammalian skin-specific promoter,
    wherein said exogenous polynucleotide expresses murine IL-18 specifically in the skin of said transgenic mouse, and
    wherein said transgenic mouse exhibits at least one symptom of atopic dermatitis.

2. The transgenic mouse of claim 1, wherein the polynucleotide encoding murine IL-18 encodes mature IL-18.

3. The transgenic mouse of claim 1, wherein the polynucleotide encoding murine IL-18 encodes mouse precursor IL-18.

4. The transgenic mouse of claim 1, wherein said mammalian promoter is a human involucrin promoter.

5. The transgenic mouse of claim 1, wherein mammalian promoter is a keratin promoter.

6. The transgenic mouse of claim 1, wherein said keratin promoter is a promoter for keratin 1, 5, 10 or 14.

7. The transgenic mouse of claim 1, wherein said exogenous polynucleotide comprises in the following order: mammalian K14 promoter, β-globin intron, PTH-mIL-18 and K14 polyA.

8. The transgenic mouse of claim 1, wherein said symptom is lichenified dermatitis.

9. The transgenic mouse of claim 1, wherein said symptom is erosive dermatitis.

10. The transgenic mouse of claim 1, wherein said symptom is inflammation associated with hyperkeratosis or acanthosis on the thick epidermis around an ulcer.

11. The transgenic mouse of claim 1, which continuously develops atopic dermatitis.

12. The transgenic mouse of claim 1, which continuously secretes IL-18 into the blood.

13. A screening method for identifying a substance that can prevent or treat atopic dermatitis comprising administering said substance to the transgenic mouse of claim 1 and determining whether a symptom of atopic dermatitis is ameliorated or prevented or determining the level(s) of IgE or histamine, or both, in the mouse.

14. The method of claim 13, wherein said substance is administered to said transgenic mouse under pathogen-free conditions.

15. The method of claim 13, wherein determining whether a symptom of atopic dermatitis has been ameliorated or prevented comprises measuring the level of mature IL-18 in the blood, detecting mature IL-18 in the skin, visual observation, microscopic observation of skin tissue, or measuring the histamine level in the blood.

16. The method of claim 13, comprising determining the level(s) of IgE or histamine, or both, in the mouse.

17. A method of making the transgenic mouse of claim 1 comprising:
a) introducing an exogenous polynucleotide comprising a murine IL-18 operably linked to a mammalian skin-specific promoter into a fertilized mouse egg, b) implanting said egg into a female mouse under conditions suitable for gestation of a transgenic mouse, and c) identifying a transgenic mouse exhibiting skin-specific expression of murine IL-18, wherein said transgenic mouse exhibits at least one symptom of atopic dermatitis.

18. A transgenic mouse whose genome contains an exogenous polynucleotide encoding murine IL-18 operably linked to a mammalian skin-specific promoter and a parathyroid leader sequence, wherein said exogenous polynucleotide expresses murine IL-18 specifically in the skin of said transgenic mouse, and wherein said transgenic mouse exhibits at least one symptom of atopic dermatitis.

19. The transgenic mouse of claim 18, wherein the mammalian skin-specific promoter is a keratin promoter.

* * * * *

UNITED STATES PATENT AND TRADEMARK OFFICE
CERTIFICATE OF CORRECTION

PATENT NO. : 7,098,373 B2
APPLICATION NO. : 10/482662
DATED : August 29, 2006
INVENTOR(S) : Hitoshi Mizutani It is certified that error appears in the above-identified patent and that said Letters Patent is hereby corrected as shown below:

Column 9, line 8, "comprising" should read --encoding --

Column10, lines 3-4, "a parathyroid leader sequence" should read --a parathyroid hormone leader sequence,--

Signed and Sealed this

Nineteenth Day of December, 2006

JON W. DUDAS
*Director of the United States Patent and Trademark Office*